(12) United States Patent
Peleg et al.

(10) Patent No.: US 11,532,244 B2
(45) Date of Patent: Dec. 20, 2022

(54) SYSTEM AND METHOD FOR ULTRASOUND SIMULATION

(71) Applicant: SIMBIONIX LTD., Airport (IL)

(72) Inventors: Yaron Peleg, Hod Hasharon (IL); Victor Levin, Rehovot (IL)

(73) Assignee: Simbionix Ltd., Airport City (IL)

( * ) Notice: Subject to any disclaimer, the term of this patent is extended or adjusted under 35 U.S.C. 154(b) by 0 days.

(21) Appl. No.: 17/023,808

(22) Filed: Sep. 17, 2020

(65) Prior Publication Data

US 2022/0084439 A1 Mar. 17, 2022

(51) Int. Cl.
| | |
|---|---|
| G09B 5/02 | (2006.01) |
| G09B 23/28 | (2006.01) |
| G01S 15/89 | (2006.01) |
| A61B 8/00 | (2006.01) |
| A61B 90/00 | (2016.01) |

(52) U.S. Cl.
CPC ........ G09B 23/286 (2013.01); G01S 15/8906 (2013.01); G09B 5/02 (2013.01); A61B 8/4254 (2013.01); A61B 2090/3762 (2016.02); G01S 15/8993 (2013.01)

(58) Field of Classification Search
None
See application file for complete search history.

(56) References Cited

U.S. PATENT DOCUMENTS

| | | |
|---|---|---|
| 5,371,778 A | 12/1994 | Yanof et al. |
| 6,283,918 B1 | 9/2001 | Kanda et al. |

(Continued)

FOREIGN PATENT DOCUMENTS

| | | |
|---|---|---|
| CN | 1874717 | 12/2006 |
| JP | H11/164833 | 6/1999 |

(Continued)

OTHER PUBLICATIONS

Wein, Wolfgang, et al. "Automatic CT-ultrasound registration for diagnostic imaging and image-guided intervention." *Medical image analysis* 12.5 (2008): 577-585.

(Continued)

*Primary Examiner* — Bruk A Gebremichael
(74) *Attorney, Agent, or Firm* — Pearl Cohen Zedek Latzer Baratz LLP

(57) ABSTRACT

Ultrasound (US) simulation systems and methods are provided, which utilize computer tomography (CT) data to generate US simulation images, offline or online. Systems and methods repeatedly derive and display consecutive US simulation images that correspond to consecutively-derived corresponding US slices (according to the changing locations and orientations of a dummy US transducer mimicking the US transducer with respect to a physical patient model)—that define geometrically US simulation regions. The US simulation images are at least partly derived from CT data using a CT to US conversion model. Acoustic parameters (e.g., tissue density, acoustic attenuation and impedance) are calculated and integrated per pixel, along beams in the US slice, to form the US image. Additional modelling may be used to calculate reflection and scattering and their effects on the image pixels, and enhancements such as animation and flow data may be added.

25 Claims, 7 Drawing Sheets

(56) References Cited

U.S. PATENT DOCUMENTS

| | | |
|---|---|---|
| 7,681,579 B2 | 3/2010 | Schwartz |
| 10,580,325 B2 | 3/2020 | Bronstein et al. |
| 2002/0191822 A1 | 12/2002 | Piper |
| 2003/0032876 A1 | 2/2003 | Chen et al. |
| 2006/0100502 A1* | 5/2006 | Chen ............... A61B 6/504 600/419 |
| 2007/0038058 A1* | 2/2007 | West ............... A61B 90/36 600/407 |
| 2007/0043285 A1 | 2/2007 | Schwartz |
| 2007/0148625 A1 | 6/2007 | Blitz et al. |
| 2008/0020362 A1 | 1/2008 | Cotin et al. |
| 2008/0187896 A1 | 8/2008 | Savitsky |
| 2009/0018808 A1 | 1/2009 | Bronstein et al. |
| 2009/0177452 A1 | 7/2009 | Ullrich et al. |
| 2009/0177454 A1 | 7/2009 | Bronstein et al. |
| 2009/0310847 A1 | 12/2009 | Matsuzaki et al. |
| 2010/0179428 A1* | 7/2010 | Pedersen ......... A61B 8/4254 600/443 |
| 2010/0272338 A1* | 10/2010 | Agnihotri ......... G16H 50/70 382/131 |
| 2011/0092804 A1 | 4/2011 | Schoenefeld et al. |
| 2017/0100092 A1* | 4/2017 | Kruse ............... G01S 15/8922 |

FOREIGN PATENT DOCUMENTS

| | | |
|---|---|---|
| JP | 2005/137455 | 6/2005 |
| JP | 2009/022733 | 2/2009 |
| JP | 2009/207677 | 9/2009 |
| WO | WO-2009/119691 | 10/2009 |

OTHER PUBLICATIONS

Wein, Wolfgang, et al. "Simulation and fully automatic multimodal registration of medical ultrasound." *International Conference on Medical Image Computing and Computer-Assisted Intervention*. Springer, Berlin, Heidelberg, 2007.

Kutter, Oliver, Ramtin Shams, and Nassir Navab. "Visualization and GPU-accelerated simulation of medical ultrasound from CT images." *Computer methods and programs in biomedicine* 94.3 (2009): 250-266.

* cited by examiner

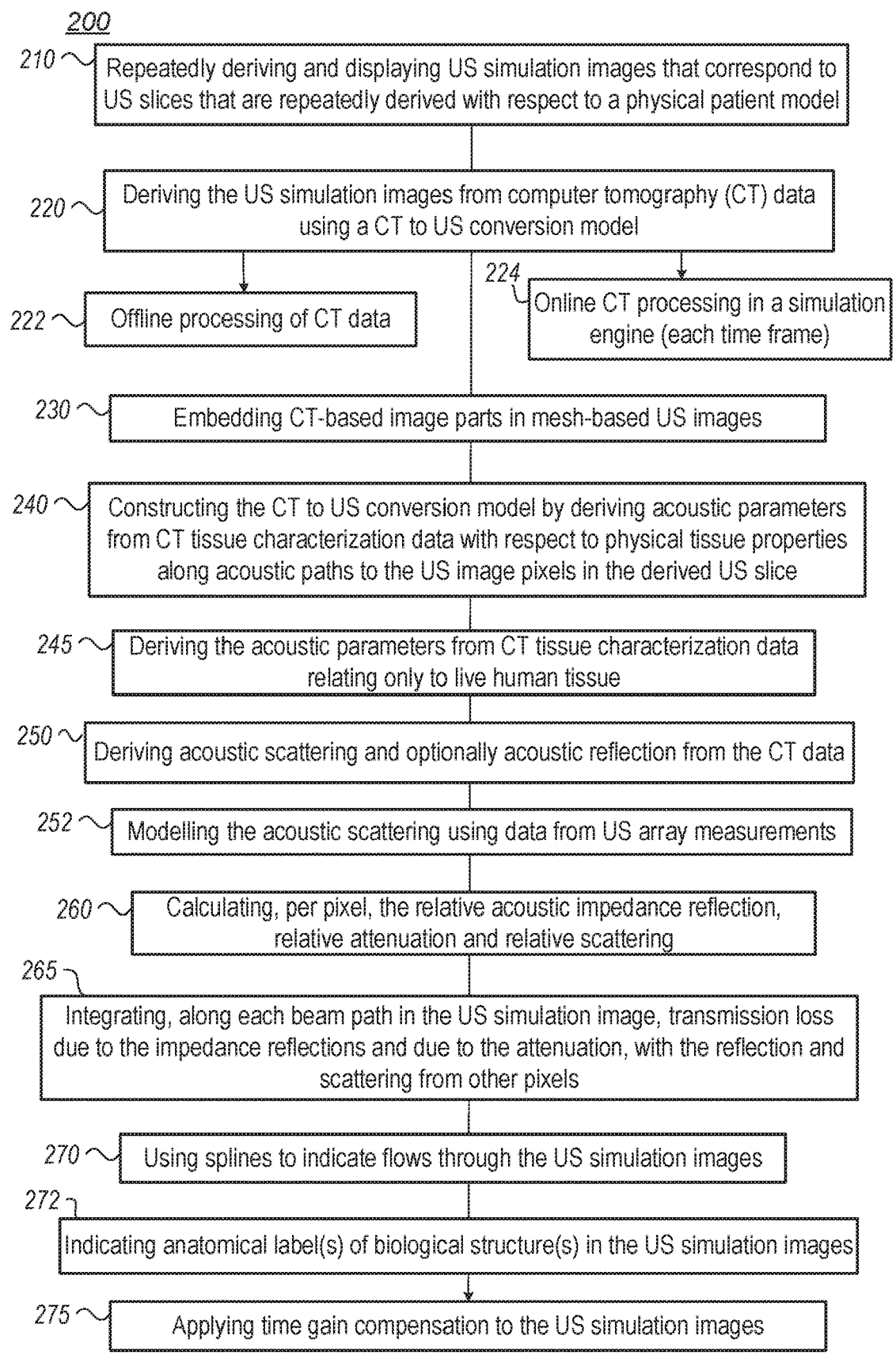
Figure 1B (Continued, 1.)

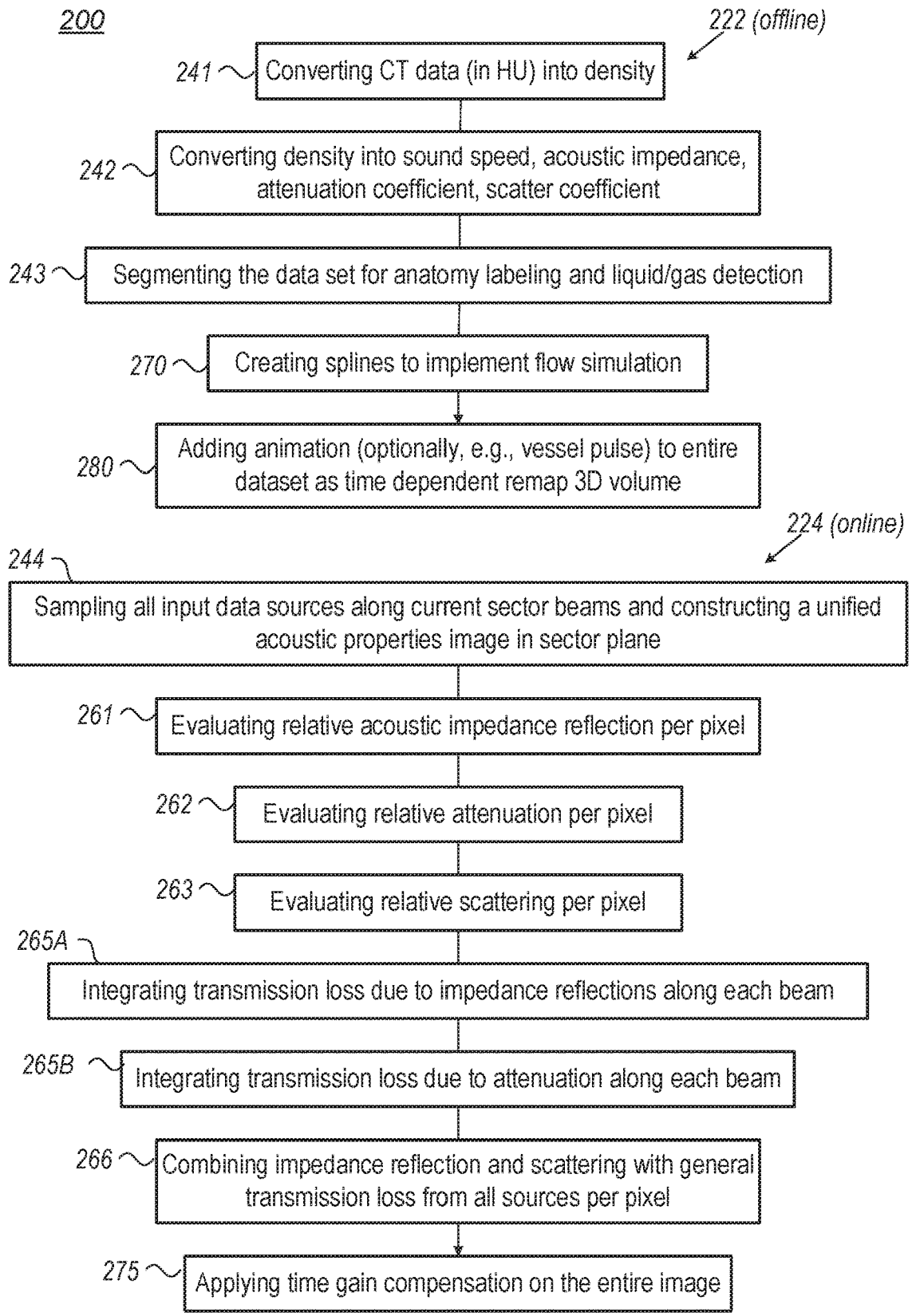
Figure 1B (continued, 2.)

SYSTEM AND METHOD FOR ULTRASOUND SIMULATION

BACKGROUND OF THE INVENTION

1. Technical Field

The present invention relates to the field of medical simulation, and more particularly, to computed tomography (CT) based ultrasound simulation.

2. Discussion of Related Art

Currently, ultrasound (US) simulation systems rely on generic, mesh-based models, which are used to generate simulated US images that relate to the position and orientation of a dummy US transducer having 6DoF (six degrees of freedom) sensors.

SUMMARY OF THE INVENTION

The following is a simplified summary providing an initial understanding of the invention. The summary does not necessarily identify key elements nor limit the scope of the invention, but merely serves as an introduction to the following description.

One embodiment of the present invention provides ultrasound (US) simulation systems that include: a physical model of at least one body part of a patient, a dummy US transducer, wherein the US simulation system is configured to repeatedly measure positions and orientations of the dummy US transducer and to consecutively derive corresponding US slices from the measured positions and orientations of the dummy US transducer with respect to the physical model, wherein the consecutive US slices define geometrically corresponding consecutive US simulation regions, and a computing device configured to repeatedly derive consecutive US simulation images that correspond to the consecutive US simulation regions from computer tomography (CT) data relating to the at least one body part using a CT to US conversion model, and to display the derived US simulation images in the corresponding US slices.

One embodiment of the present invention provides US simulation methods that include: repeatedly measuring positions and orientations of a dummy US transducer with respect to a physical model of at least one body part of a patient, consecutively deriving corresponding US slices from the repeatedly measured positions and orientations of the dummy US transducer, wherein the consecutive US slices define geometrically corresponding consecutive US simulation regions, repeatedly deriving consecutive US simulation images that correspond to the consecutive US simulation regions from computer tomography (CT) data relating to the at least one body part using a CT to US conversion model, and displaying the derived US simulation images in the corresponding US slices.

One embodiment of the present invention provides US simulation systems that include: a computing device comprising: a memory; and one or more processors configured to: repeatedly receive positions and orientations of a dummy US transducer with respect to a physical model of at least one body part of a patient, consecutively derive corresponding US slices from the repeatedly received positions and orientations of the dummy US transducer, wherein the consecutive US slices define geometrically corresponding consecutive US simulation regions, and repeatedly derive consecutive US simulation images that correspond to the consecutive US simulation regions from computer tomography (CT) data relating to the at least one body part using a CT to US conversion model.

These, additional, and/or other embodiments and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1A:
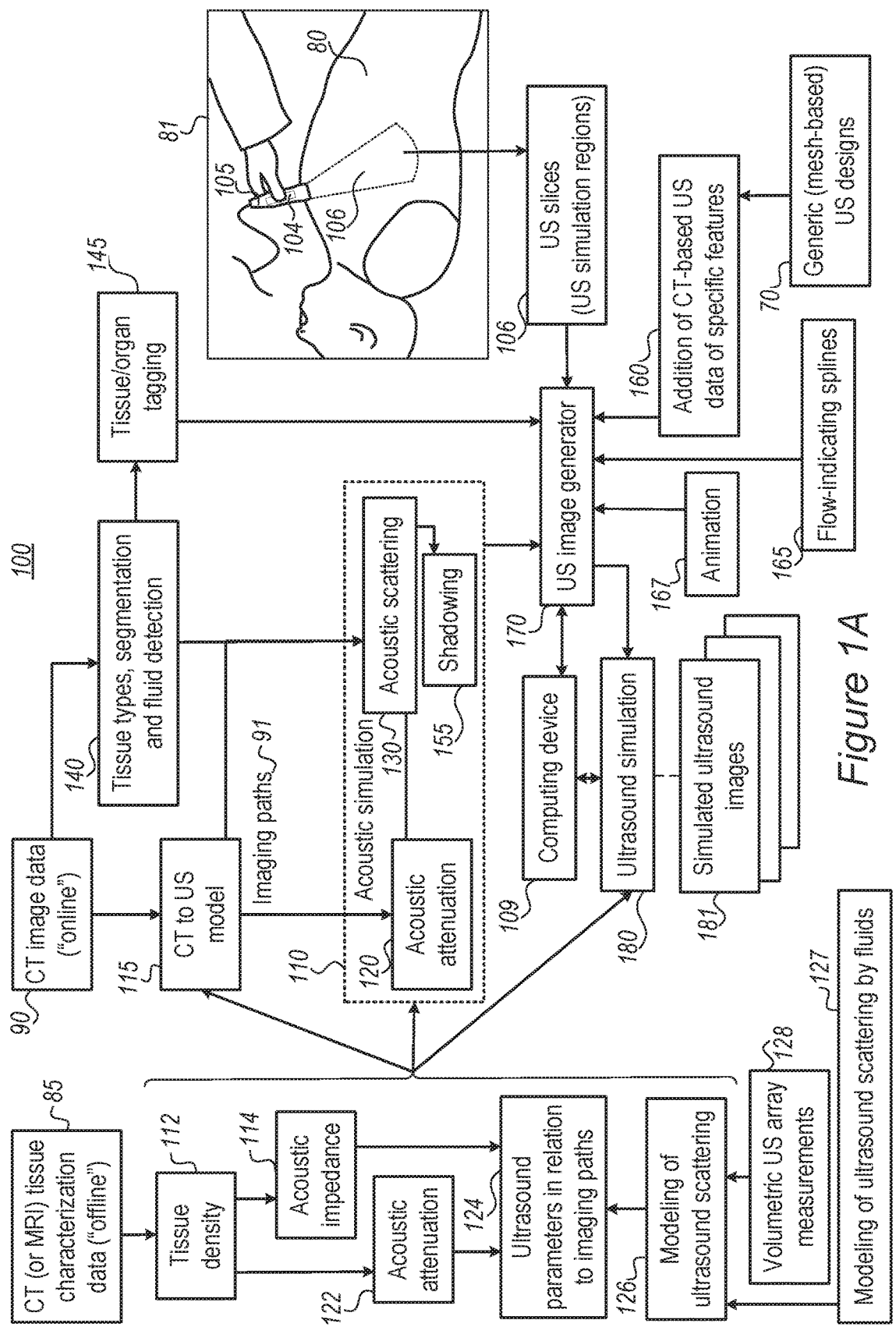
FIG. 1A is a high-level schematic block diagram of ultrasound (US) simulation systems, according to some embodiments of the invention.

In the following description, various embodiments of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual embodiments of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing", "deriving" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention provide efficient and economical methods and mechanisms for providing ultrasound simulation and may thereby provide improvements to the technological field of medical simulation. Ultrasound (US) simulation systems and methods are provided, which utilize computer tomography (CT) data to generate US simulation images, offline or online. Systems and methods repeatedly derive and display consecutive US simulation images that correspond to consecutively-derived corresponding US slices (according to the changing locations and orientations of a dummy US transducer mimicking the US transducer with respect to a physical patient model)—that define geometrically US simulation regions. The US simulation images are at least partly derived from CT data using a CT to US conversion model. Acoustic parameters (e.g., tissue density, acoustic attenuation and impedance) are calculated and integrated per pixel, along beams in the US slice, to form the US image. Additional modelling may be used to calculate reflection and scattering and their effects on the image pixels, and enhancements such as animation and flow data may be added.

Figure 1B:
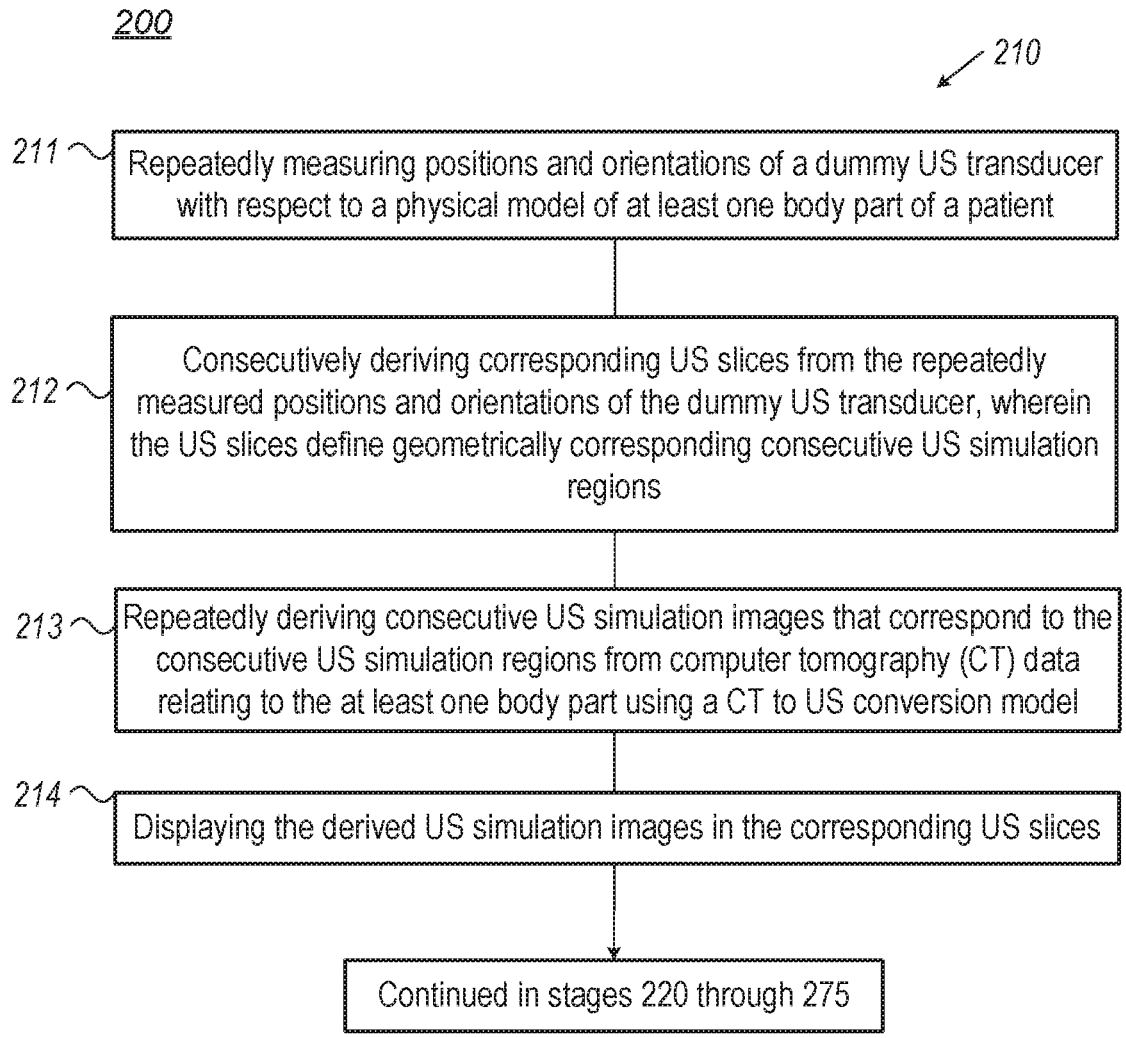
FIG. 1B is a high-level flowchart illustrating US simulation methods, according to some embodiments of the invention.
Figure 1C:
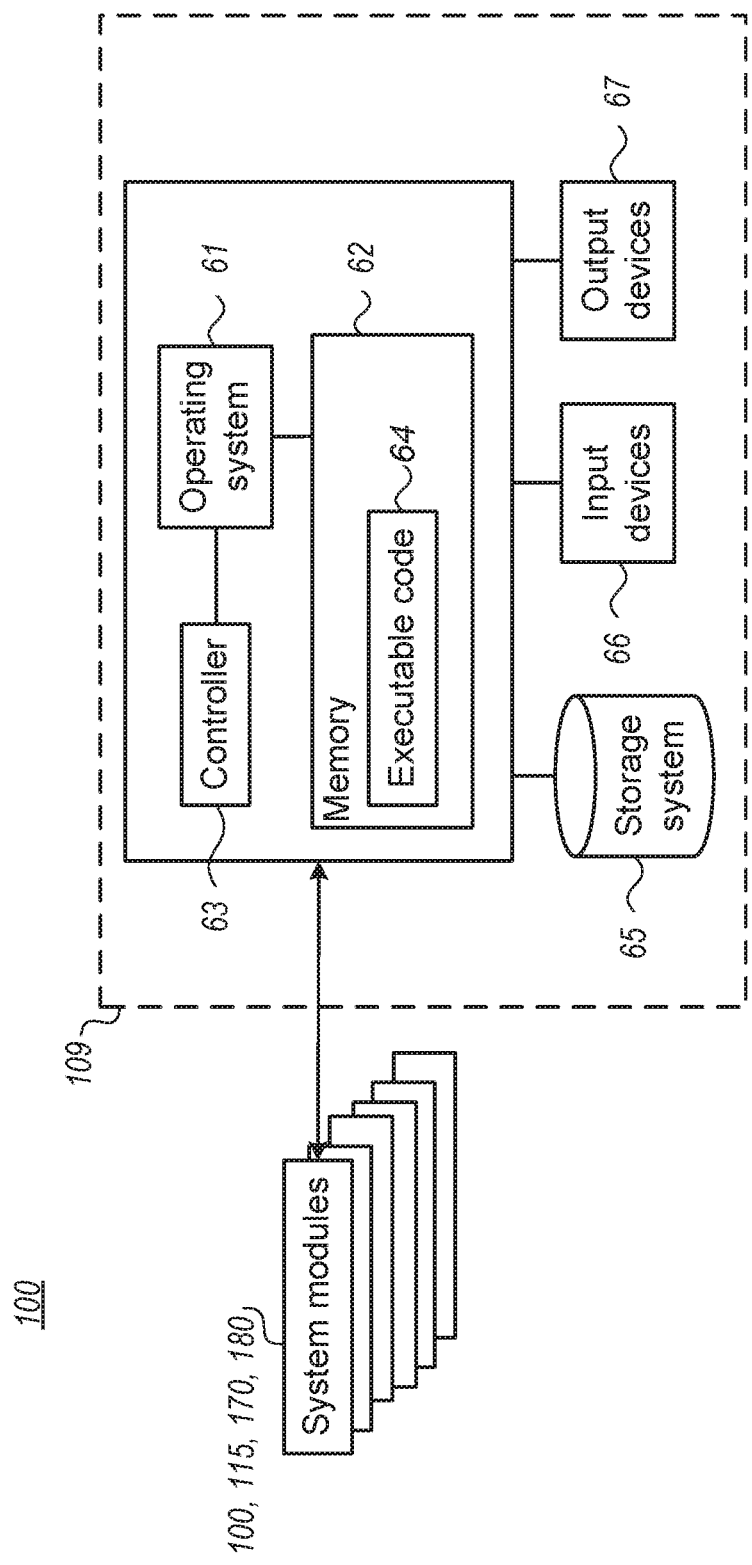
FIG. 1C is a high-level block diagram of an exemplary computing device, which may be used with embodiments of the present invention.
Figure 2A:
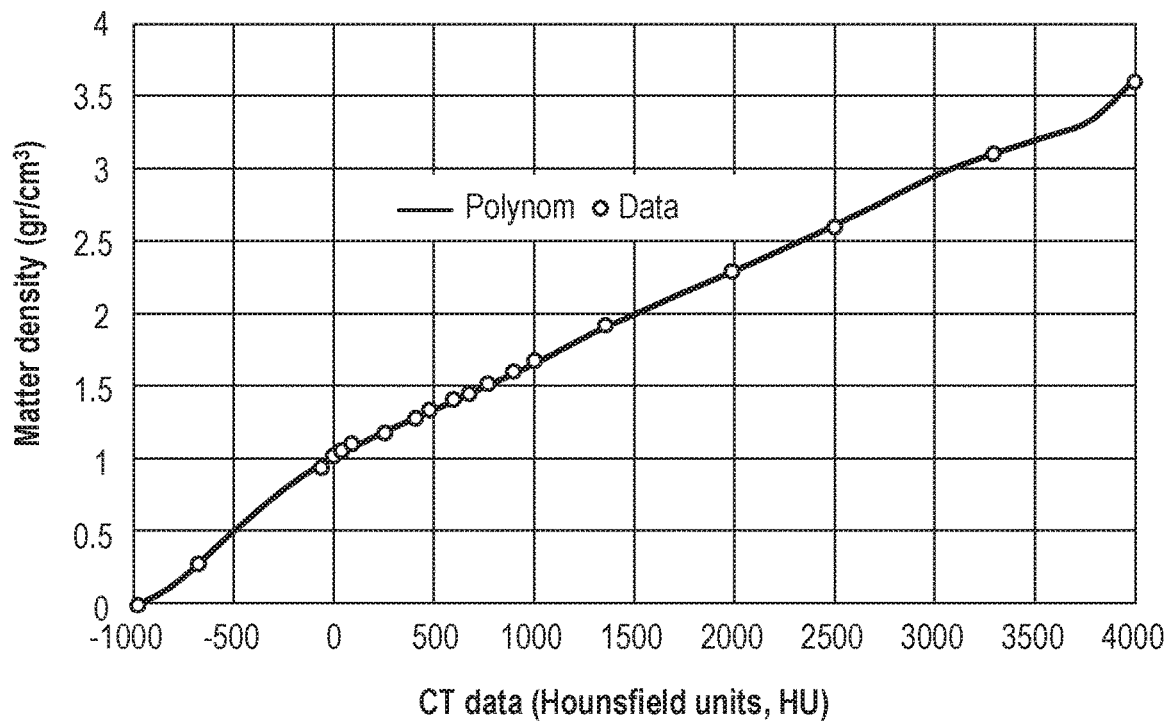
FIGS. 2A-2D are high-level schematic examples for relations between CT data and simulated US data, according to some embodiments of the invention.
Figure 2B:
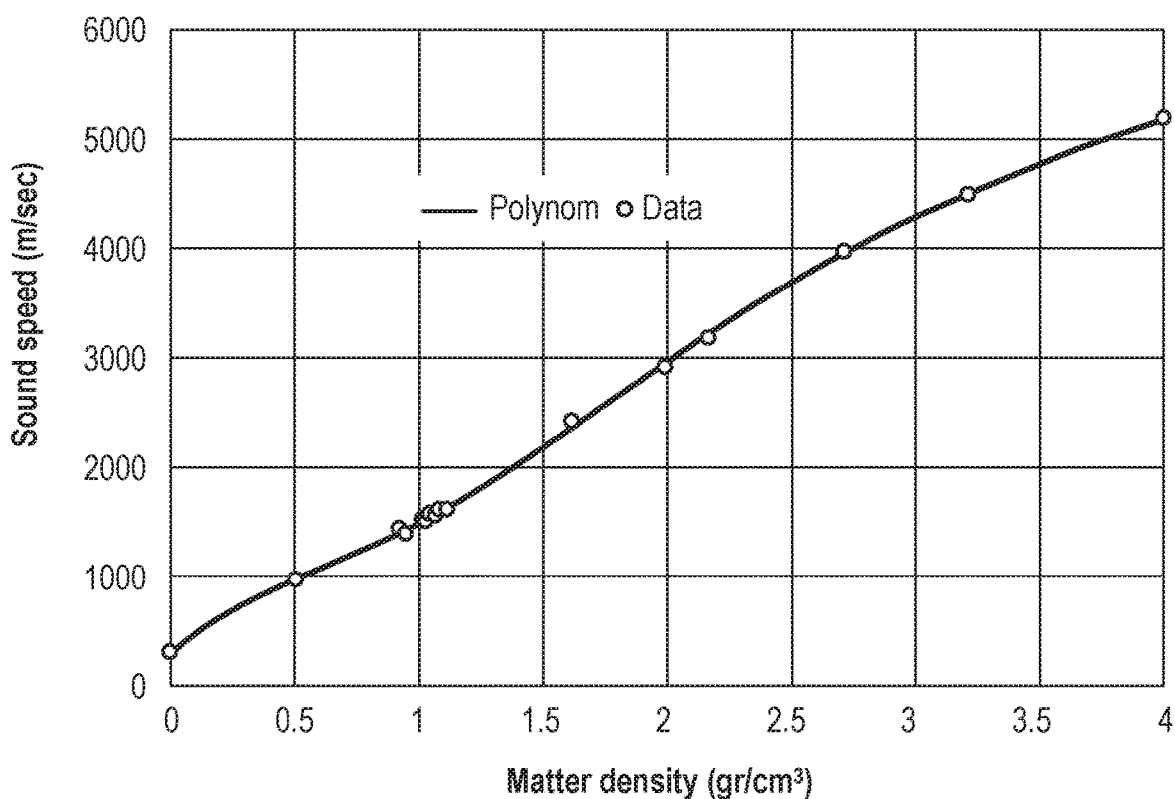
Figure 2C:
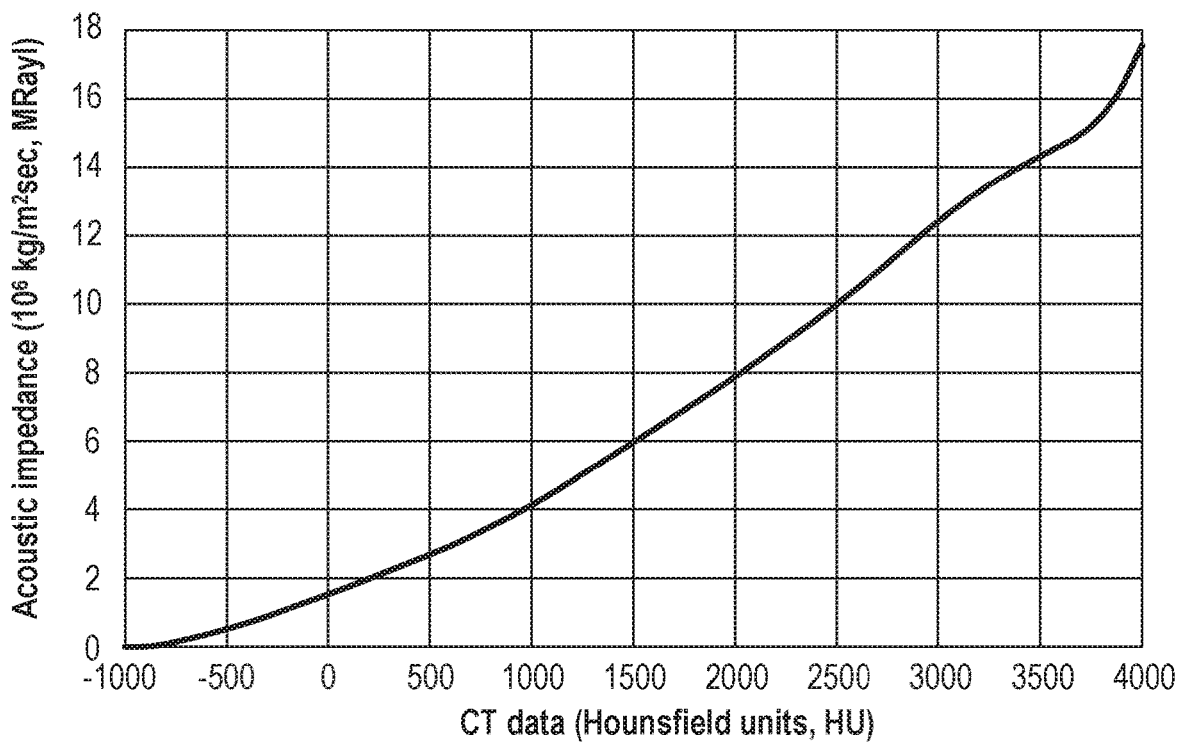
Figure 2D:
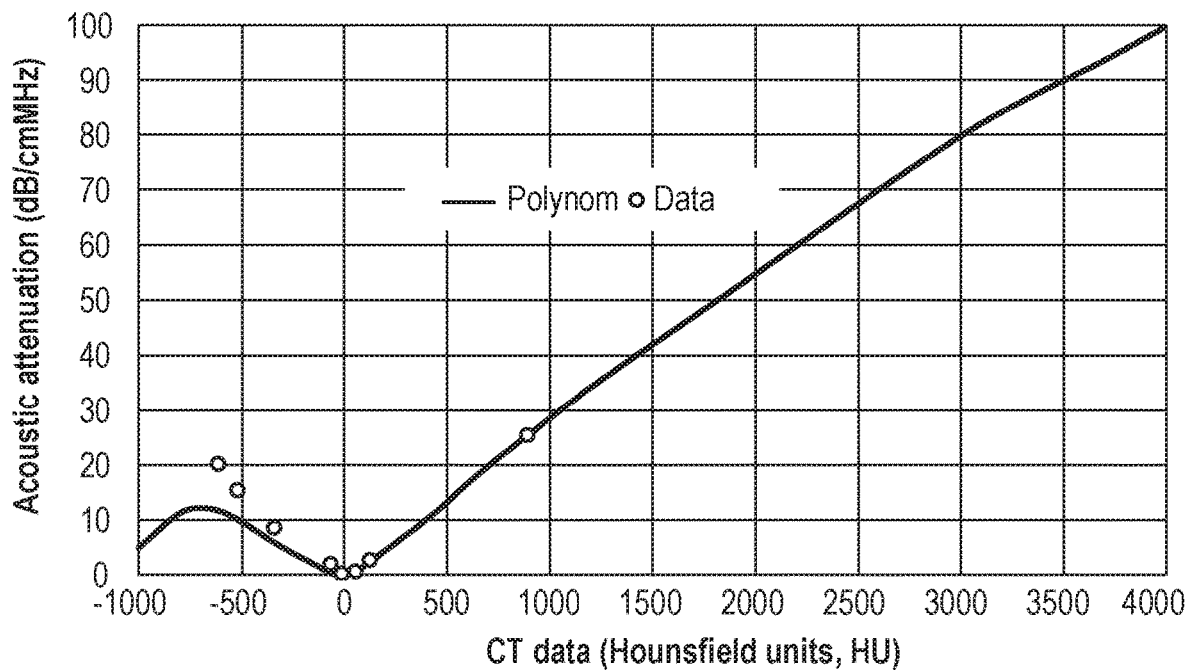

FIG. 1A is a high-level schematic block diagram of ultrasound (US) simulation systems 100, according to some embodiments of the invention. FIG. 1B is a high-level flowchart illustrating US simulation methods 200, according to some embodiments of the invention. FIG. 1C is a high-level block diagram of exemplary computing device 109, which may be used with embodiments of the present invention. FIGS. 2A-2D are high-level schematic examples for relations between CT data and simulated US data, according to some embodiments of the invention. FIG. 2A provides a schematic example for the relation between the tissue density and CT data in Hounsfield units (HU). FIG. 2B provides a schematic example for the relation between the speed of sound in the tissue and the tissue density. FIG. 2C provides a schematic example for the relation between the tissue acoustic impedance and CT data in Hounsfield units (HU) and FIG. 2D provides a schematic example for the relation between the tissue acoustic attenuation and CT data in Hounsfield units (HU), according to some embodiments of the invention.

As illustrated schematically in FIG. 1A, ultrasound (US) simulation system 100 may include, in a training setting 81, a physical model 80 (e.g., a dummy, or a mannequin) of at least one body part of a patient (e.g., torso or part thereof, with or without the extremities and head, and/or parts thereof) and a dummy US transducer 105.

US simulation system 100 may be configured to simulate any type of US transducer, e.g., linear, convex, phased-array or other types of US transducers, including US transducers for external and/or internal use. Dummy US transducer 105 may include a dummy US probe of any type, such as linear, convex, phased-array or other types of US transducers, US transducers for external or internal use. Dummy US transducer 105 may be configured to resemble in shape, weight and feel of any type of US transducers, specifically of the simulated US transducer. It is noted however, that in some embodiments, dummy US transducer 105 may have any shape, size or structural characteristics, and is not limited to imitations of a US transducer. Dummy US transducer 105 typically does not act as an actual US transducer, but rather simulates for a user the external feel of a real US transducer.

US simulation system 100 may be configured to measure positions and orientations of physical dummy US transducer 105 with respect to physical model 80 such as a dummy representing a patient or parts thereof. US simulation system 100 may be configured to consecutively (e.g., repeatedly or iteratively) derive corresponding US slices 106 (illustrated schematically) from the measured positions and orientations of physical dummy US transducer 105 with respect to physical model 80. US slices 106 may define geometrically US simulation regions in which US simulation images are to be embedded, with respect to the physical dummy. The US simulation images presented in or projected on US slices 106 simulate real US images that would have been received from a real patient at corresponding locations, but are based on and are derived from CT data, as explained herein. Over a series of repeats or iterations, multiple US slices 106 may be produced as dummy US transducer 105 is moved over physical model 80, defining multiple US simulation regions. Over a series of repeats or iterations, the US images are derived and displayed according to the respectively defined US simulation regions in US slices 106. Typically, as dummy US transducer 105 is moved over physical model 80, consecutive US images are shown with respect to the corresponding US slices 106 defined by the positions and orientations of physical dummy US transducer 105.

US slices 106 may include flat two-dimensional slices or surfaces that define corresponding consecutive US simulation regions, geometrically with respect to the measured (changing) positions and orientations of physical dummy US transducer 105 and with respect to physical model 80 to correspond to the actual US slices that would have been measured by a real US transducer at the measured position and orientation on a real patient, with respect to the corresponding simulated type of US transducer. US slices 106 may have axial, lateral and elevational dimensions that correspond to the simulated type of US transducer. The focal points and orientations of US slices 106 may be determined from the measured positions and orientations of physical dummy US transducer 105. US slices 106 may represent US simulation regions in two dimensions, representing corresponding slices of physical model 80, or representing the body part modeled by physical model 80. A series of US slices 106 may be assembled to create a three-dimensional (3D) image.

For example, dummy US transducer 105 may have, e.g., a 6 DoF (six degrees of freedom) sensor 104 (illustrated schematically) that is used to measure the location and orientation of dummy US transducer 105. In certain embodiments, the location and orientation of dummy US transducer 105 may be measured in other ways, such as using tracker(s), camera(s) with image processing software, etc., which are considered herein as being equivalent in this respect to 6 DoF sensor(s) 104. US simulation system 100 is configured to repeatedly and consecutively derive US slices 106 from measurements or measured positions of dummy US transducer 105, e.g., by 6 DoF sensor 104 and/or tracking, with respect to physical model 80 and with respect to movements of dummy US transducer 105.

US simulation system 100 includes a computing device 109 (see FIG. 1C below) configured to repeatedly derive and display consecutive US simulation images 181 that correspond to the consecutive US simulation regions with respect to the body part(s) of physical model 80 and simulating its internal structure as would be observable by ultrasound, providing a trainee with ultrasound simulation 180. US simulation images 181 are derived so that they match the position and orientation of corresponding US slice 106 to which they are applied with respect to its geometric dimensions and according to respective body part. Over a series of repeats or iterations, consecutive US simulation images 181 may be derived and displayed according to corresponding consecutive US slices 106 so that as dummy US transducer 105 is moved over physical model 80, consecutive US images 181 are displayed with respect to the corresponding (current) US slice 106 defined by the (current) position and orientation of physical dummy US transducer 105.

US simulation images 181 are at least partly derived by a US image generator 170 from computer tomography (CT) data 90 relating to the body part(s), using a CT to US conversion model 115. US simulation images 181 may be derived by US simulation system 100 to correspond to any type of US transducer, such as linear, convex, phased-array or other types of US transducers.

It is noted that the repeated derivation of US slices 106 and of US simulation images 181 may be carried out at specified rates and/or with respect to movements of dummy US transducer 105 which require updating US slices 106. Consecutively-derived US slices 106 may correspond to or be derived from consecutive positions and orientations of dummy US transducer 105 with respect to physical model 80 and consecutively-derived US simulation images 181 may correspond to changes in US slices 106 and/or to changes in user preferences such as changing in imaging parameters that may be applied to regular (e.g., real) US images. Upon such changes, US simulation system 100 may update US simulation images 181 correspondingly.

In certain embodiments, US simulation images 181 may be mesh-based 70 (e.g., generic) and comprise an added part 160 that is imaged using CT to US conversion model 115. For example, specific regions of interest for practice, such as specific anatomical structures, tumors, etc. may be modeled according to specific CT data and embedded (160) within a more generic US simulation model, such as a mesh-based model.

In certain embodiments, US simulation system 100 may operate based on offline CT tissue characterization data 85 and/or based on online CT image data 90. Certain embodiments may comprise CT-based US simulations prepared in advance by analyzing CT tissue characterization data 85. Correspondingly, CT to US conversion model 115 may be constructed from CT tissue characterization data 85 offline, prior to displaying US simulation images 181.

In certain embodiments, US simulation system 100 may operate based on real-time conversion of CT image data 90 to US simulation data, performing the conversion within time frames which may be few, tens or hundreds of milliseconds long. Correspondingly, CT to US conversion model 115 may be constructed from CT data 90 online, on a frame-by-frame basis during the displaying of US simulation images 181. For example, each US simulated image 181 may be derived within a specified time frame, followed by the derivation of next US simulated image 181 within the next time frame. Time frames may range between 1 ms to 100 ms, e.g., time frames may be few ms long, few tens of ms long, few hundreds of ms long, or have intermediate, possible variable durations. For example, in certain embodiments. US simulation system 100 may operate at about 30 FPS (frames per second), or possibly at rates of 20, 40, 50, 60 FPS or intermediate values. An optimization process may be applied to balance the computational complexity with the required frame rate. For example, a target frame rate may be used to restrict the computational complexity, or certain computationally-heavy algorithms may be carried out at a slower rate and be used to provide occasional updates at a lower frame rate, while maintaining the target frame rate.

Yet other embodiments may combine these two operation modes in various ways, such as providing both modes and/or utilizing data and relations derived from CT tissue characterization data 85 in the offline mode to enhance the online mode. For example, CT to US model 115 may comprise data and/or relations derived from CT tissue characterization data 85 and used to enhance online US simulation from CT image data 90. e.g., by speeding up the conversion, providing more details at specific regions, handling difficult tissue regions, etc.

Non-limiting examples for offline CT data processing by US simulation system 100 comprise converting CT tissue characterization data 85 into tissue density 112, converting tissue density 112 into acoustic parameters such as sound speed, acoustic impedance 114, attenuation coefficients 122, scatter coefficients, etc., segmenting 140 the data set for anatomy labeling 145 and liquid/gas detection, creating splines 165 (e.g., curves that indicate flow, such as derived by spline interpolation)—to implement flow simulation and possible adding animation 167 (e.g., vessel pulse) to the entire dataset as time dependent remap 3D volume to yield US simulation images 181. It is noted that various methods for flow simulation may be used, such as splines, synthetic 3D flow vector fields or even runtime physical flow simulation, as well as any equivalent flow simulation method.

Online CT data processing by US simulation system 100 may be performed in a simulation engine (e.g., using computing device 109), possibly operating frame by frame of simulated US images 181. Non-limiting examples for online CT data processing by US simulation system 100 comprise sampling all input data sources (e.g., converted CT data set/sets 90, optionally meshes 70 and/or splines 165) along current sector beams 106 and imaging paths 91 thereof, and constructing unified acoustic properties 110 for image pixels in sector planes 106. For example, US simulation system 100 may be configured (e.g., using computing device 109 and relative to the tissue type) to evaluate relative acoustic impedance reflection per pixel, to evaluate relative attenuation 120 per pixel, to evaluate relative scattering 130 per pixel, etc., and to integrate the transmission loss due to impedance reflections along each beam 91, to integrate transmission loss due to attenuation along each beam 91 and to combine impedance reflection and scattering with general transmission loss from all (or possibly some, or most) sources (scattered US from other pixels) per pixel of simulated US image 181, and applying time gain compensation on entire image 181.

In various embodiments, CT to US conversion model 115 may be configured to apply different resolutions for different parts of the simulated US slice, with respect. e.g., to the type of simulated tissue, depth of the simulated pixel, specific features of the CT image and the CT resolution. It is noted that while typical CT resolution is in the scale of millimeters (typically 4-2 mm, rarely down to 0.2 mm for long-exposure CT), typical US resolution is in the scale of tenths of millimeters (typically 0.5-0.1 mm, rarely less than 0.1 mm for high frequency probes). However, resolution requirements in US also depend on the depth of the imaged pixel into the tissue and moreover, beam interaction with the tissue may be simulated at different scales. For example, CT to US conversion model 115 may be configured to have sufficient pixels along the simulated US beam to simulate the real effects of tissue-US beam interactions. Specifically, attenuation and scattering may be evaluated on a relatively coarser resolution since they are depth dependent and can be corrected accordingly, while impedance reflection and sharp surface reflection may be evaluated on a relatively finer scale since they relate to boundary effects. For example, segmentation and surface data may be used to reach US simulation at an adequate resolution. CT to US conversion model 115 may be configured to provide sufficient US resolution by data simulation based in the CT data, e.g., by addition of high-frequency noise to the converted CT data at the corresponding US regions.

CT to US conversion model 115 may include acoustic properties and parameters 110 that are derived from CT tissue characterization data 85 and/or from CT data 90 with respect to physical tissue properties along acoustic imaging paths 91 (also termed "beams") to the US image pixels (corresponding to spatial locations) in derived US slice 106. In various embodiments, acoustic simulation 110 and/or parameters thereof that are used to construct CT to US conversion model 115 offline may be derived from CT tissue characterization data 85 relating only to live human tissue. Advantageously, the inventors have found out that, while much of the CT tissue characterization data available in the literature was measured on animals or on non-living tissue, removing this data and retaining only CT tissue characterization data 85 that was measured on live human tissue provided a much more accurate and reliable CT to US model 115.

Embodiments for deriving acoustic simulation parameters 124 and/or CT to US model 115 are described herein, which may be used for either or both offline and online operation of US simulation system 100. Steps of example procedures are exemplified in FIGS. 2A-2D, which illustrate derived relations between CT and US data, according to some embodiments of the invention.

CT tissue characterization data 85 typically includes 3D data sets of scanned tissue volumes that provide X-ray radiation absorption per voxel, calibrated and measured in Hounsfield units (HU). The derivation of US relevant data and/or CT to US model 115 from CT tissue characterization data 85 and/or CT image data 90 may include any of (i) a correlation of CT data to tissue material density (see example in FIG. 2A), (ii) a correlation of the speed of sound to the tissue material density (see example in FIG. 2B), (iii) a literature-based functional relation between tissue material density and the CT data (see example in FIG. 2C) and (iv) a derived and approximated relation between acoustic attenuation and the CT data (see example in FIG. 2D).

FIG. 2A illustrates an example experimental correlation between CT tissue characterization data 85 and density 112 of tissue matter (for organic tissues) that is based on empirical data (measured on live human tissue).

FIG. 2B illustrates an example experimental correlation between the speed of sound in organic tissue materials and tissue material density 112 that is based on empirical data (measured on live human tissue). Optimally, the correlation may be derived to hold for a wide range of densities 112 starting from air (externally, surrounding the patient and internally, in air bubbles) and ending with most dense bones in the body. The correlation was found to be adequate for at least most of the tissue types that are required for ultrasound simulation.

FIG. 2C illustrates an example selective literature-based correlation between acoustic impedance 114 and CT tissue characterization data 85, which was derived by cross-referencing measurement data from various public sources to derive functions for calculating tissue matter density 112 as a function of the CT signal in HU, and for calculating the sound speed (S) as a function of the matter density—and to derive therefrom a polynomial relating the acoustic impedance (Z) as a function of HU. It is noted that while the acoustic impedance for most soft tissue types is between 1.4-1.8 MRayl ($10^6$ kg/m$^2$ sec), bones (having a porous structure) and different types of cartilage and teeth exhibit a wider range of acoustic impedance values.

FIG. 2D illustrates an example selective literature-based correlation between acoustic attenuation 122 (A) and CT tissue characterization data 85, which was derived by cross-referencing measurement data from various public sources, and used to provide US parameters 124 from acoustic attenuation 122 in relation to the imaging path to each voxel and the US frequency that is simulated. The approximation was carried out only with respect to data pertaining to live human tissue, as the inventors have noted that the difference in physical character of dead tissue or animal tissue is reflected in the corresponding CT data and does not provide satisfactory acoustic characterization data. The selection was proved to be difficult, due to the scarcity and incoherency of the researched literature sources. Advantageously, the inventors have found out that retaining only CT tissue characterization data 85 that was measured on live human tissue provided a much more accurate and reliable CT to US model 115.

Acoustic scattering 126 may be modelled in various ways, including (i) a constant percentage of energy loss due to acoustic attenuation 122, possibly manually calibrated using live ultrasound images 90 as a reference, (ii) using MRI data or other means (e.g., manual adjustment) to directly model ultrasound scattering by fluids 127 and/or (iii) using volumetric US array measurements 128 to characterize US scattering by various types of tissues and/or structures. For example, additional supporting data used for the US image generation may be derived from 2D or 3D US array measurements that provide direct measurements of US dispersion for specific tissue and organ types, and/or from MRI data, especially relating to liquid and gas in the images. The distinction between tissue types and free fluids may be used to generate US simulation of flows (e.g., blood or air flow). The CT-based US simulation may be used to provide the full US simulation, or to provide US simulation of specific regions within a generic US simulation, e.g., CT-based US simulation of specific organs or tumors, implanted overriding the generic model.

Derived ultrasound parameters 124 may be saved as 3D data or texture files (e.g., in DDS format), and used directly to derive ultrasound simulation 180 at US image generator 170 and/or to provide CT to US model 115 for online applications. Alternatively or complementarily, ultrasound parameters 124 may be used to enhance acoustic simulation 110 in one or more aspects during online operation.

In certain embodiments, in either online or offline operation modes, US simulation system 100 may be configured to derive (e.g., by computing device 109) the acoustic parameters in acoustic simulation 110 from the CT data using a polynomial model. The acoustic parameters may include tissue density and related sound speeds, acoustic impedances, attenuation coefficients and scatter coefficients. For example, the acoustic parameters may comprise acoustic attenuation 120, 122, acoustic impedance 114, acoustic scattering 130 and optionally acoustic reflection, from which shadowing 155 may be derived. Scattering and reflection may be modelled using identified structures or tissue types (e.g., according to tissue density 112) and/or using data from volumetric US array measurements 128 for characterizing scattering and reflection from various tissue types.

Acoustic dispersion may be derived from a combination of the physical characterization from the CT data and further analysis aimed at distinguishing tissue types and segmentation into tissue and organ types in the imaged region. Both the scattering coefficient of the respective voxel and borders between tissue and organ types may be used to simulate the spatial dispersion of US and its effects on the resulting simulated US image (e.g., reflections, shadowing, etc.). Some volumetric noise may be added over the modelled US derived from the processed CT data—to simulate typical ultrasound image features.

In certain embodiments, in either online or offline operation modes. US simulation images 181 may be derived by calculating (e.g., by computing device 109), per pixel (and relative to the tissue type): a relative acoustic impedance reflection, a relative attenuation and a relative scattering, and integrating, along each beam path in US simulation image 181, transmission loss due to the impedance reflections and due to the attenuation, with the reflection and scattering from other pixels.

In certain embodiments, in either online or offline operation modes, US simulation system 100 may be configured to identify (e.g., by computing device 109) tissue types 140 in the CT data (either offline or online) and provide segmentation data that may be used in US simulation images 181. e.g., for tagging tissue types and/or organs 145 in US simulation images 181. US simulation system 100 may be further configured to indicate (e.g., by computing device 109) at least one anatomical label of at least one biological structure in US simulation images 181.

US simulation system 100 may be configured to identify fluids, and in certain embodiments, US simulation images 181 may further comprise splines 165 configured to indicate flows through images 181. Since fluid provide significantly different US frequency-acoustic attenuation dependence than tissue, US simulation system 100 may be configured to differentiate fluids from tissue voxels, e.g., using segmentation. Segmentation data may be used to construct flow splines, either automatically or manually (with the user providing the flow direction and speed).

US simulation system 100 may be configured to apply (e.g., by computing device 109) time gain compensation (TGC, increasing signal for more remote pixels to overcome ultrasound attenuation and correct for the distances from the transducer) to US simulation images 181. It is noted that while TGC is typically applied in real ultrasound image processing, in disclosed embodiments US simulation system 100 may be configured to apply the image correction in advance, imitating TGC to reach similar image improvement.

FIG. 1B is a high-level flowchart illustrating an ultrasound (US) simulation method 200, according to some embodiments of the invention. The example method stages may be carried out with respect to US simulation system 100 described above, and/or one or more processors, which may be configured to implement US simulation method 200; alternatively, other equipment may be used. Method 200 may be at least partially implemented by at least one computer processor, such as computing device 109 described herein, or one or more processors. Certain embodiments comprise computer program products comprising a computer readable storage medium having computer readable program embodied therewith and causing one or more processors configured to be configured to carry out the relevant stages of method 200. Method 200 may comprise the following stages, irrespective of their order.

US simulation method 200 may include repeatedly deriving and displaying consecutive US simulation images that correspond to repeatedly derived consecutive US slices (e.g. flat two-dimensional slices or surfaces with respect to a physical patient model that define corresponding US simulation regions) (stage 210), wherein the US simulation images are at least partly derived from computer tomography (CT) data using a CT to US conversion model (stage 220). Stage 210 may comprise repeatedly measuring positions and orientations of a dummy US transducer with respect to a physical model of at least one body part of a patient (stage 211), consecutively deriving corresponding US slices (e.g., in each iteration or repeat, deriving another slice) from the repeatedly measured positions and orientations of the dummy US transducer, wherein the consecutive US slices define geometrically corresponding consecutive US simulation regions (stage 212), repeatedly deriving (e.g., in each iteration or repeat, deriving another image) consecutive US simulation images that correspond to the consecutive US simulation regions from computer tomography (CT) data relating to the at least one body part using a CT to US conversion model (stage 213), and displaying repeatedly-derived consecutive US simulation images in corresponding US slices (stage 214). For example, on each iteration a slice may be derived, and a corresponding (e.g., corresponding in the sense they are correlated to the same location in the body, or that they are derived in the same iteration) image may be derived, and the image may be placed or projected on the slice.

In certain embodiments, US simulation method 200 may include constructing the CT to US conversion model from CT tissue characterization data offline, prior to displaying the US simulation images (stage 222). In certain embodiments. US simulation method 200 may comprise constructing the CT to US conversion model from CT data online, on a frame-by-frame basis during the displaying of the US simulation images (stage 224), with respect to time frames that correspond to different US images. Examples for offline processing of the CT data (stage 222) and for online CT processing, e.g., using a simulation engine applied each time frame (stage 224) are disclosed in more detail below.

US simulation method 200 may include embedding or inserting at least one image part derived using the CT to US conversion model—into mesh-based US simulation images (stage 230). For example, specific regions of interest for practice, such as specific anatomical structures, tumors, etc. may be modeled according to specific CT data and embedded within, e.g., combined with or added to, a more generic US simulation model, such as a mesh-based model.

US simulation method 200 may include constructing the CT to US conversion model by deriving acoustic parameters from the CT data with respect to physical tissue properties along acoustic paths to the US image pixels in the derived US slice (stage 240).

In certain embodiments, deriving of the acoustic parameters 240 may be carried out from CT tissue characterization data relating only to live human tissue (stage 245). In certain embodiments, deriving of the acoustic parameters 240 may comprise deriving acoustic attenuation from the CT data using a polynomial model (stage 245). In certain embodiments, deriving of the acoustic parameters 240 may comprise deriving acoustic scattering and optionally acoustic reflection from the CT data (stage 250).

US simulation method 200 may include modelling the acoustic scattering using data from US array measurements (stage 252), e.g., configured to provide direct 2D or 3D measurements of acoustic scattering.

In certain embodiments, deriving of the US simulation images 210 may be carried out by calculating, per pixel of the US image and/or per voxel of the CT data (and relative to the tissue type): a relative acoustic impedance reflection, a relative attenuation and a relative scattering (stage 260), and integrating, along each beam path in the US simulation image, transmission loss due to the impedance reflections and due to the attenuation, with the reflection and scattering from other pixels (stage 265).

US simulation method 200 may further comprise using splines to indicate flows through the US simulation images (stage 270). Splines may comprise curves used to indicate flows that are derived by spline interpolation, or curves derived by other computational procedures or received from external source(s).

US simulation method 200 may further comprise indicating at least one anatomical label of at least one biological structure in the US simulation images (stage 272).

US simulation method 200 may further comprise applying time gain compensation to the US simulation images (stage 275).

In certain embodiments, offline processing of the CT data (stage 222) may comprise converting the CT data (in Hounsfield units. HU) into density data (stage 241) and converting the density data into sound speed data, acoustic impedance data, attenuation coefficient data and/or scatter coefficient data (stage 242). e.g., per pixel and/or per regions or parts of the CT data. Offline processing of the CT data 222 may further comprise segmenting the data set for anatomy labeling and/or liquid or gas detection (stage 243) and optionally creating splines to implement flow simulation (stage 270). In certain embodiments, offline processing of the CT data 222 may further comprise adding animation (e.g., vessel pulse) to the entire dataset as time dependent remap 3D volume.

In certain embodiments, online CT processing, e.g., using a simulation engine applied. e.g., each time frame (stage 224) may comprise sampling all input data sources (e.g., converted CT data set/sets, meshes and splines) along current sector beams and constructing a unified acoustic properties image in sector plane (stage 244), evaluating the relative acoustic impedance reflection, e.g., per pixel (stage 261), evaluating relative attenuation, e.g., per pixel (stage 262) and evaluating relative scattering, e.g., per pixel (stage 263), and then integrating transmission loss due to impedance reflections, e.g., along each beam (stage 265A), integrating transmission loss due to attenuation, e.g., along each beam (stage 265B). Finally, online CT processing 224 may comprise combining impedance reflection and scattering data with the general transmission loss from some or all sources (scattered US from other pixels) per pixel (stage 268) and optionally applying time gain compensation (TGC) on the entire image or regions thereof.

Advantageously, disclosed US simulation systems 100 and methods 200 utilize computer tomography (CT) or other medical imaging data to derive more detailed, voxel-based, tissue specific and possibly patient-specific US simulation. Disclosed systems 100 and methods 200 apply sophisticated CT to US modelling methods which rely on selected data and approximation methods which do not require prior art assumptions such as linear functional relations among parameters, constant speed of sound, limited modelling and other assumptions, which limited the accuracy and applicability of CT to US modelling. Instead, disclosed methods apply intensity mapping and realistic ultrasound physical calculations based on evaluated acoustical properties of examined medium, as derived from the CT data. Specifically, the acoustic properties may be generated from real CT image datasets obtained by regular medical CT imaging systems scanning live patients, which correspondingly may enable ultrasound simulation of real clinical cases. Disclosed systems 100 and methods 200 fully integrate CT to US modelling into operative US simulation systems that can operate based on offline or online analysis and that allow combinations of mesh-based and CT-based US simulation. US simulation systems 100 may use real size human mannequins and life-like probes tracked in 3D space to generate appropriate simulated ultrasound images, which may be generated entirely on GPU.

FIG. 1C is a high-level block diagram of exemplary computing device 109, which may be used with embodiments of the present invention. One or more computing devices 109 may be used. Computing device 109 may include one or more processors or controllers 63 that may be or include, for example, one or more central processing unit processor(s) (CPU), one or more Graphics Processing Unit (s) (GPU or general purpose GPU—GPGPU), a chip or any suitable computing or computational device, an operating system 61, a memory 62, a storage 65, input devices 66 and output devices 67. US simulation system 100, operating online and/or offline. CT to US modelling 115, acoustic simulation 110 and/or any of the system modules such as US image generator 170 and US simulation 180 may be or be executed by computing device 109 and/or may comprise at least parts of the computer system as shown for example in FIG. 1C.

Operating system 61 may be or may include any code segment designed and/or configured to perform tasks involving coordination, scheduling, arbitration, supervising, controlling or otherwise managing operation of computing device 109, for example, scheduling execution of programs. Memory 62 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 62 may be or may include a plurality of, possibly different memory units. Memory 62 may store for example, instructions to carry out a method (e.g., code 64), and/or data such as user responses, interruptions, etc.

Executable code 64 may be any executable code, e.g., an application, a program, a process, task or script. Executable code 64 may be executed by controller 63 possibly under control of operating system 61. For example, executable code 64 may when executed cause the production or compilation of computer code, or application execution such as VR execution or inference, according to embodiments of the present invention. Executable code 64 may be code produced by methods described herein. For the various modules and functions described herein, one or more computing devices 109 or components of computing device 109 may be used. Devices that include components similar or different to those included in computing device 109 may be used, and may be connected to a network and used as a system. One or more processor(s) 63 may be configured to carry out embodiments of the present invention by for example executing software or code, and may act as modules and computing device described herein.

Storage 65 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code. VR model data, parameters, etc. may be stored in a storage 65 and may be loaded from storage 65 into a memory 62 where it may be processed by controller 63. In some embodiments, some of the components shown in FIG. 1C may be omitted.

Input devices 66 may be or may include for example a mouse, a keyboard, a touch screen or pad or any suitable input device. It will be recognized that any suitable number of input devices may be operatively connected to computing device 109 as shown by block 66. Output devices 67 may include one or more displays, speakers and/or any other suitable output devices. It will be recognized that any suitable number of output devices may be operatively connected to computing device 109 as shown by block 67. Any applicable input/output (I/O) devices may be connected to computing device 109, for example, a wired or wireless network interface card (NIC), a modem, printer or facsimile machine, a universal serial bus (USB) device or external hard drive may be included in input devices 66 and/or output devices 67.

Embodiments of the invention may include one or more article(s) (e.g., memory 62 or storage 65) such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein, or configure the processor to carry out such methods.

Embodiments of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment". "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. An ultrasound (US) simulation system comprising:
  a physical model of at least one body part of a patient,
  a dummy US transducer, and
  one or more processors configured to:
    repeatedly measure positions and orientations of the dummy US transducer and to consecutively derive corresponding US slices from the measured positions and orientations of the dummy US transducer with respect to the physical model, wherein the consecutive US slices define geometrically corresponding consecutive US simulation regions, and repeatedly derive consecutive US simulation images that correspond to the consecutive US simulation regions from computer tomography (CT) data relating to the at least one body part using a CT to US conversion model, and to display the derived US simulation images in the corresponding US slices, wherein the CT to US conversion model comprises acoustic parameters derived from CT tissue characterization data with respect to physical tissue properties along acoustic paths to US image pixels in the derived US slice, wherein the acoustic parameters comprise tissue density and related sound speeds, acoustic impedances, attenuation coefficients and scatter coefficients, and wherein the US simulation images are derived by:
   calculating, per given pixel, and relative to a tissue type: a relative acoustic impedance reflection, a relative attenuation and a relative scattering, and
   integrating, along each beam path in the US simulation image, transmission loss due to the impedance reflections and due to the attenuation, with the reflection and scattering from pixels other than the given pixel.

2. The US simulation system of claim 1, wherein the dummy US transducer has a 6 DoF (six degrees of freedom) sensor and wherein the US slices are derived from measurements by the 6 DoF sensor with respect to the physical model and with respect to movements of the dummy US transducer.

3. The US simulation system of claim 1, wherein the US simulation images are mesh-based and comprise a part that is imaged using the CT to US conversion model.

4. The US simulation system of claim 1, wherein the CT to US conversion model is constructed from CT tissue characterization data offline, prior to displaying the US simulation images.

5. The US simulation system of claim 1, wherein the CT to US conversion model is constructed from CT data online, on a frame-by-frame basis during the displaying of the US simulation images.

6. The US simulation system of claim 1, wherein the CT to US conversion model is derived from CT tissue characterization data relating only to live human tissue.

7. The US simulation system of claim 6, wherein the acoustic parameters comprise acoustic attenuation derived from the CT tissue characterization data using a polynomial model.

8. The US simulation system of claim 7, wherein the acoustic parameters further comprise acoustic scattering and optionally acoustic reflection.

9. The US simulation system of claim 8, wherein the acoustic scattering is further modeled using data from US array measurements.

10. The US simulation system of claim 1, wherein the US simulation images further comprise splines configured to indicate flows therethrough.

11. The US simulation system of claim 1, wherein the computing device is further configured to indicate at least one anatomical label of at least one biological structure in the US simulation images.

12. The US simulation system of claim 1, wherein the computing device is further configured to apply time gain compensation to the US simulation images.

13. An ultrasound (US) simulation method comprising:
repeatedly measuring positions and orientations of a dummy US transducer with respect to a physical model of at least one body part of a patient, consecutively deriving corresponding US slices from the repeatedly measured positions and orientations of the dummy US transducer, wherein the consecutive US slices define geometrically corresponding consecutive US simulation regions, repeatedly deriving consecutive US simulation images that correspond to the consecutive US simulation regions from computer tomography (CT) data relating to the at least one body part using a CT to US conversion model, and displaying the derived US simulation images in the corresponding US slices, wherein the method further comprises constructing the CT to US conversion model by deriving acoustic parameters from the CT data with respect to physical tissue properties along acoustic paths to US image pixels in the derived US slice, and wherein the deriving of the US simulation images is carried out by:
   calculating, per given pixel and relative to a tissue type: a relative acoustic impedance reflection, a relative attenuation and a relative scattering, and
   integrating, along each beam path in the US simulation image, transmission loss due to the impedance reflections and due to the attenuation, with the reflection and scattering from pixels other than the given pixel.

14. The US simulation method of claim 13, wherein the US simulation images are mesh-based and the method further comprises embedding therein at least one image part derived using the CT to US conversion model.

15. The US simulation method of claim 13, wherein the CT to US conversion model is constructed from CT tissue characterization data offline, prior to displaying the US simulation images.

16. The US simulation method of claim 13, wherein the CT to US conversion model is constructed from CT data online, on a frame-by-frame basis during the displaying of the US simulation images.

17. The US simulation method of claim 13, wherein the deriving of the acoustic parameters is carried out from CT data relating only to live human tissue.

18. The US simulation method of claim 17, wherein the deriving of the acoustic parameters comprises deriving acoustic attenuation from the CT data using a polynomial model.

19. The US simulation method of claim 18, wherein the deriving of the acoustic parameters comprises deriving acoustic scattering and optionally acoustic reflection from the CT data.

20. The US simulation method of claim 19, further comprising modelling the acoustic scattering using data from US array measurements.

21. The US simulation method of claim 13, further comprising using splines to indicate flows through the US simulation images.

22. The US simulation method of claim 13, further comprising indicating at least one anatomical label of at least one biological structure in the US simulation images.

23. The US simulation method of claim 13, further comprising applying time gain compensation to the US simulation images.

24. An ultrasound (US) simulation system comprising: a computing device comprising:
a memory; and
a processor configured to:
repeatedly receive positions and orientations of a dummy US transducer with respect to a physical model of at least one body part of a patient,
consecutively derive corresponding US slices from the repeatedly received positions and orientations of the dummy US transducer, wherein the consecutive US slices define geometrically corresponding consecutive US simulation regions, and
repeatedly derive consecutive US simulation images that correspond to the consecutive US simulation regions from computer tomography (CT) data relating to the at least one body part using a CT to US conversion model,
wherein the processor is further configured to construct the CT to US conversion model by deriving acoustic parameters from the CT data with respect to physical tissue properties along acoustic paths to US image pixels in the derived US slice, and
wherein the deriving of the US simulation images is carried out by:
calculating, per given pixel and relative to a tissue type: a relative acoustic impedance reflection, a relative attenuation and a relative scattering, and
integrating, along each beam path in the US simulation image, transmission loss due to the impedance reflections and due to the attenuation, with the reflection and scattering from pixels other than the given pixel.

25. The US simulation system of claim 24, wherein the deriving of the acoustic parameters is carried out from CT data relating only to live human tissue.

* * * * *